(12) United States Patent
Bunn

(10) Patent No.: US 12,733,901 B2
(45) Date of Patent: Sep. 15, 2026

(54) ARTIFICIAL INTELLIGENCE SYSTEM FOR COMPREHENSIVE MEDICAL DIAGNOSIS, PROGNOSIS, AND TREATMENT OPTIMIZATION THROUGH MEDICAL IMAGING

(71) Applicant: Ultrasound AI, Inc., Highlands Ranch, CO (US)

(72) Inventor: Robert S Bunn, Highlands Ranch, CO (US)

(73) Assignee: Ultrasound AI, Inc., Greenwood Village, CO (US)

( * ) Notice: Subject to any disclaimer, the term of this patent is extended or adjusted under 35 U.S.C. 154(b) by 14 days.

(21) Appl. No.: 18/603,191

(22) Filed: Mar. 12, 2024

(65) Prior Publication Data

US 2024/0215945 A1 Jul. 4, 2024

Related U.S. Application Data

(63) Continuation-in-part of application No. 17/573,246, filed on Jan. 11, 2022, now Pat. No. 11,969,289,
(Continued)

(51) Int. Cl.
*A61B 5/00* (2006.01)
*A61B 8/00* (2006.01)
(Continued)

(52) U.S. Cl.
CPC .............. *A61B 8/0866* (2013.01); *A61B 8/06* (2013.01); *A61B 8/0875* (2013.01);
(Continued)

(58) Field of Classification Search
CPC ......... A61B 8/06; A61B 8/0875; A61B 8/467; A61B 8/488; G06T 2207/10132;
(Continued)

(56) References Cited

U.S. PATENT DOCUMENTS 8,828,981 B2 9/2014 Creasy et al.
10,650,929 B1 5/2020 Beck et al.
(Continued)

FOREIGN PATENT DOCUMENTS

CN 110613480 A 12/2019
IN 201941040741 A 4/2021
(Continued)

OTHER PUBLICATIONS

CN 202180043378.8, Response to first office action issued Dec. 28, 2023, dated May 10, 2024.
(Continued)

*Primary Examiner* — Joel F Brutus
(74) *Attorney, Agent, or Firm* — VLP Law Group LLP; David J. Thibodeau

(57) ABSTRACT

Systems and methods for comprehensive medical diagnosis, prognosis, and treatment optimization are provided. A neural network is trained on a large dataset of medical images or raw data from various imaging modalities, such as ultrasound, MRI, CT, and X-ray, which are labeled with ground truth diagnoses of a wide range of medical conditions. The trained neural network can then be provided with medical images of a patient, and the neural network can make predictions and provide insights related to the presence, absence, severity, progression, or risk of various medical conditions. These predictions and insights can support clinical decision-making and enable early intervention, personalized treatment, and improved patient outcomes. The system can be continually updated with new data to improve its performance over time, and can be integrated into healthcare workflows to enhance the accuracy, efficiency, and effectiveness of medical diagnosis and treatment.

17 Claims, 2 Drawing Sheets

Related U.S. Application Data which is a continuation of application No. PCT/US2021/038164, filed on Jun. 20, 2021, and a continuation of application No. 17/352,290, filed on Jun. 19, 2021, now Pat. No. 11,266,376.

(60) Provisional application No. 63/451,844, filed on Mar. 13, 2023, provisional application No. 63/041,360, filed on Jun. 19, 2020.

(51) Int. Cl.

| | |
|---|---|
| ***A61B 8/06*** | (2006.01) |
| ***A61B 8/08*** | (2006.01) |
| ***G06T 7/00*** | (2017.01) |
| ***G06T 7/20*** | (2017.01) |
| ***G16H 10/60*** | (2018.01) |
| ***G16H 30/20*** | (2018.01) |
| ***G16H 30/40*** | (2018.01) |
| ***G16H 50/20*** | (2018.01) |

(52) U.S. Cl.

CPC ........... *A61B 8/0883* (2013.01); *A61B 8/467* (2013.01); *A61B 8/488* (2013.01); *G06T 7/0016* (2013.01); *G06T 7/20* (2013.01); *G16H 10/60* (2018.01); *G16H 30/20* (2018.01); *G16H 30/40* (2018.01); *G16H 50/20* (2018.01); *G06T 2207/10132* (2013.01); *G06T 2207/20081* (2013.01); *G06T 2207/30008* (2013.01); *G06T 2207/30044* (2013.01); *G06T 2207/30048* (2013.01); *G06T 2207/30104* (2013.01)

(58) Field of Classification Search

CPC .......... G06T 2207/20081; G06T 2207/30009; G06T 2207/30048

See application file for complete search history.

(56) References Cited

U.S. PATENT DOCUMENTS

| | | | |
|---|---|---|---|
| 11,266,376 | B2 | 3/2022 | Bunn |
| 11,969,289 | B2 | 4/2024 | Bunn |
| 12,318,249 | B2 | 6/2025 | Bunn |
| 2004/0236193 | A1 | 11/2004 | Sharf |
| 2006/0241510 | A1 | 10/2006 | Halperin et al. |
| 2009/0093717 | A1 | 4/2009 | Carneiro et al. |
| 2009/0169074 | A1 | 7/2009 | Avinash et al. |
| 2010/0312115 | A1 | 12/2010 | Dentinger |
| 2011/0248818 | A1 | 10/2011 | Hashim-Waris |
| 2012/0135427 | A1 | 5/2012 | Kypros et al. |
| 2014/0018678 | A1 | 1/2014 | Donnelly et al. |
| 2014/0089004 | A1 | 3/2014 | Frey et al. |
| 2015/0148657 | A1 | 5/2015 | Shashar et al. |
| 2015/0342560 | A1 | 12/2015 | Davey et al. |
| 2016/0071266 | A1 | 3/2016 | Srivastava et al. |
| 2016/0228505 | A1 | 8/2016 | Stossel et al. |
| 2016/0340407 | A1 | 11/2016 | Hodi et al. |
| 2017/0000683 | A1 | 1/2017 | Samec et al. |
| 2017/0086785 | A1 | 3/2017 | Bjaerum |
| 2017/0091402 | A1 | 3/2017 | Salafia et al. |
| 2017/0216335 | A1 | 8/2017 | Mangano |
| 2017/0357844 | A1 | 12/2017 | Comaniciu et al. |
| 2018/0032666 | A1 | 2/2018 | Sun et al. |
| 2018/0153504 | A1 | 6/2018 | Herickhoff et al. |
| 2018/0247410 | A1 | 8/2018 | Madabhushi et al. |
| 2019/0008674 | A1 | 1/2019 | Myers et al. |
| 2019/0021698 | A1 | 1/2019 | Raghvan et al. |
| 2019/0034590 | A1 | 1/2019 | Oren et al. |
| 2019/0154704 | A1 | 5/2019 | Davis et al. |
| 2019/0209116 | A1 | 7/2019 | Sjostrand et al. |
| 2019/0246904 | A1 | 8/2019 | Kim et al. |
| 2019/0251638 | A1 | 8/2019 | Braz et al. |
| 2019/0367987 | A1 | 12/2019 | Hamamah et al. |
| 2020/0005899 | A1 | 1/2020 | Nicula et al. |
| 2020/0005901 | A1 | 1/2020 | Cohen et al. |
| 2020/0022674 | A1 | 1/2020 | Egorov |
| 2020/0035362 | A1* | 1/2020 | Abou Shousha ...... G06N 3/096 |
| 2020/0069292 | A1 | 3/2020 | Abolmaesumi et al. |
| 2020/0077947 | A1 | 3/2020 | Shi et al. |
| 2020/0147006 | A1 | 5/2020 | Charney et al. |
| 2020/0149110 | A1 | 5/2020 | Targan et al. |
| 2020/0168310 | A1 | 5/2020 | Westin et al. |
| 2020/0170614 | A1 | 6/2020 | Kim et al. |
| 2021/0068905 | A1 | 3/2021 | Quaid et al. |
| 2021/0090254 | A1 | 3/2021 | Gong et al. |
| 2021/0118559 | A1 | 4/2021 | Lefkofsky |
| 2021/0128115 | A1 | 5/2021 | Mapiye et al. |
| 2021/0217166 | A1 | 7/2021 | Graule et al. |
| 2021/0287513 | A1 | 9/2021 | Mazar et al. |
| 2021/0307702 | A1 | 10/2021 | Moon |
| 2021/0393235 | A1 | 12/2021 | Bunn |
| 2022/0028551 | A1 | 1/2022 | Jordan et al. |
| 2022/0067922 | A1 | 3/2022 | Yu |
| 2022/0133260 | A1 | 5/2022 | Bunn |
| 2022/0133280 | A1 | 5/2022 | Urabe et al. |
| 2022/0164635 | A1 | 5/2022 | Johansen et al. |
| 2022/0192501 | A1 | 6/2022 | Shuler |
| 2022/0328189 | A1 | 10/2022 | Zhou et al. |
| 2022/0400963 | A1 | 12/2022 | Bucklet et al. |
| 2023/0172580 | A1 | 6/2023 | Bunn et al. |
| 2024/0173011 | A1 | 5/2024 | Bunn |
| 2024/0173012 | A1 | 5/2024 | Bunn |
| 2024/0197287 | A1 | 6/2024 | Bunn |
| 2025/0275747 | A1 | 9/2025 | Bunn |

FOREIGN PATENT DOCUMENTS

| | | | |
|---|---|---|---|
| JP | 2018-140172 | A | 9/2018 |
| KR | 1020200013161 | A | 2/2020 |
| WO | 2020/061590 | A1 | 3/2020 |
| WO | 2020107023 | A1 | 5/2020 |

OTHER PUBLICATIONS

CN 202180043378.8, Rejection Decision issued May 18, 2024.

CN 202180043378.8, Response to Rejection Decision iissued May 18, 2024, dated Aug. 19, 2024.

EP 21825348.2 EESR Issued Jun. 18, 2024.

Oelze et al., "Review of Quantitative Ultrasound: Envelope Statistics and Backscatter Coefficient Imaging and Contributions to Diagnostic Ultrasound", IEEE Transactions on Ultrasonics, Ferroelectrics, and Frequency Control, IEEE, USA, vol. 63, No. 2, Feb. 1, 2016 (Feb. 1, 2016), pp. 336-351, XP011597293, ISSN: 0885-3010, DOI: 10.1109/TUFFC.2015.2513958 [retrieved on Jan. 29, 2016].

Suff Natalie et al: "The prediction of preterm delivery: What is new?", Seminars in Fetal and Neonatal Medicine, Elsevier, GB, vol. 24, No. 1, Sep. 28, 2018 (Sep. 28, 2018), pp. 27-32, XP085591331, ISSN: 1744-165X, DOI: 10.1016/J.SINY.2018.09.006.

Pizzella Stephanie et al: "Evolving cervical imaging technologies to predict preterm birth", Seminars in Immunopathology, Springer Berlin Heidelberg, Berlin/Heidelberg, vol. 42, No. 4, Jun. 10, 2020 (Jun. 10, 2020), pp. 385-396, XP037251810, ISSN: 1863-2297, DOI: 10.1007/S00281-020-00800-5 [retrieved on Jun. 10, 2020].

Andrea Campagner, #., Luisa Agnello, #., Carobene, A., Padoan, A., Del Ben, F., Locatelli, M., . . . Marcello Ciaccio, #. (2025). Complete Blood Count and Monocyte Distribution Width-Based Machine Learning Algorithms for Sepsis Detection: Multicentric Development and External Validation Study. J. Med. Internet Res., 40009841. Retrieved from https://pubmed.ncbi.nlm.nih.gov/40009841.

Beauchamp, N. J., Bryan, R. N., Bui, M. M., Krestin, G. P., McGinty, G. B., Meltzer, C. C., & Neumaier, M. (2023). Integrative diagnostics: the time is now—a report from the International Society for Strategic Studies in Radiology. Insights Imaging, 14(1), 1-13. doi: 10.1186/s13244-023-01379-9.

(56) References Cited

OTHER PUBLICATIONS

C-AILM https://ifcc.org/ifcc-emerging-technologies-division/etd-committees/wg-aigd/.
C-ID https://www.eflm.eu/site/who-we-are/divisions/science-division/fu/c-integrative-diagnostics.
Cesselli, D., Ius, T., Isola, M., Del Ben, F., Da Col, G., Bulfoni, M., Skrap, M. (2019). Application of an Artificial Intelligence Algorithm to Prognostically Stratify Grade II Gliomas. Cancers, 31877896. Retrieved from https://pubmed.ncbi.nlm.nih.gov/31877896.
Da Col, G., Del Ben, F., Bulfoni, M., Turetta, M., Gerratana, L., Bertozzi, S., . . . Cesselli, D. (2022). Image Analysis of Circulating Tumor Cells and Leukocytes Predicts Survival and Metastatic Pattern in Breast Cancer Patients. Front. Oncol., 35223462. Retrieved from https://pubmed.ncbi.nlm.nih.gov/35223462.
Del Ben, F. (2025). Beyond test results: the strategic importance of metadata for the integration of AI in laboratory medicine. Clin. Chern. Lab. Med., 39846365. Retrieved from https://pubmed.ncbi.nlm.nih.gov/39846365.
Del Ben, F., Biasizzo, J., & Curcio, F. (2019). A fast, nondestructive, low-cost method for the determination of hematocrit of dried blood spots using image analysis. Clin. Chern. Lab. Med., 30179847. Retrieved from https://pubmed. ncbi.nl m.nih.gov/30179847.
Del Ben, F., Da Col. G., Cobarzan, D., Turetta, M., Rubin, D., Buttazzi, P., & Antico, A. (2023). A fully interpretable machine learning model for increasing the effectiveness of urine screening. Am. J. Clin. Pathol., 37658807. Retrieved from https://pubmed.ncbi.nlm.nih.gov/37658807.
Fabris, M., Del Ben, F., Sozio, E., Beltrami, A. P., Cifii, A., Bertolino, G., . . . Curcio, F. (2022). Cytokines from Bench to Bedside: A Retrospective Study Identifies a Definite Panel of Biomarkers to Early Assess the Risk of Negative Outcome in COVID-19 Patients. Int. J. Mol. Sci., 35563218. Retrieved from https://pubmed.ncbi.nlm.nih.gov/35563218.
Soldati, G., Del Ben, F., Brisotto, G., Biscontin, E., Bulfoni, M., Piruska, A., . . . Mea, V. D. (2018). Microfluidic droplets 1 2 content classification and analysis through convolutional neural networks in a liquid biopsy workflow. Am. J. Transl. Res., 30662646. Retrieved from https://pubmed.ncbi.nlm.nih.gov/30662646.
Sorace, J., Aberle, D. R., Elimam, D., Lawvere, S., Tawfik, 0., & Wallace, W. D. (2012). Integrating pathology and radiology disciplines: an emerging opportunity? BMC Med., 10(1), 1-6. doi: 10.1186/1741-7015-10-100.
Wild, R., Sozio, E., Margiotta, R. G., Dellai, F., Acquasanta, A., Del Ben, F., . . . Laio, A. (2024). Maximally informative feature selection using Information Imbalance: Application to COVID-19 severity prediction. Sci. Rep., 38730063. Retrieved from https://pubmed.ncbi.nlm.nih.gov/38730063.
CN 202180043378.8, Response to Rejection Decision issued May 18, 2024, dated Aug. 19, 2024.
International Preliminary Report on Patentability received for PCT Patent Application No. PCT/US2021/038164, mailed on Dec. 29, 2022, 9 pages.
International Preliminary Report on Patentability received for PCT Patent Application No. PCT/US2023/011845, mailed on Aug. 8, 2024, 12 pages.
Office Action dated Sep. 3, 2024 regarding Application No. JP2022-574786.
Office Action dated Oct. 21, 2024 regarding Application No. KR10-2023-7000075.
Response to Office Action dated Nov. 19, 2024 regarding Application No. JP2022-574786.
Response to Office Action dated Dec. 23, 2024 regarding Application No. KR10-2023-7000075.
Response to Office Action dated Dec. 30, 2024 regarding Application No. EP21825348.2.
Office Action dated Feb. 4, 2025 regarding Application No. JP2022-574786.
Office Action Issued in related Chinese Patent Application No. 202180043378.8 issued Dec. 28, 2023, 27 pages.
PCT/US21/38164 International Search Report and Written Opinion, mailed Sep. 30, 2021.
PCT/US23/011845 International Search Report and Written Opinion, mailed Apr. 27, 2023.
PCT/US24/014349 International Search Report and Written Opinion, mailed May 7, 2024.
PCT/US24/019803 International Search Report and Written Opinion, mailed Jun. 17, 2024.
PCT/US24/014353 International Search Report and Written Opinion, mailed May 7, 2024.
PCT/US24/014356 International Search Report and Written Opinion, mailed May 9, 2024.
Kuo et al., "Automation of the kidney function prediction and classification through ultrasoundbased kidney imaging using deep learning." In: npj Digital Medicine vol. 2, Article No. 29 (2019), [onlinel [retrieved on Apr. 17, 2024 (Apr. 17, 2024)] Retrieved from the Internet <URL: https://www.nature.com/articles/s41746-019-0104-2#ethics>.
Diniz Pedro H. et al: "Deep Learning Strategies for Ultrasound in Pregnancy", EMJ Reproductive Health, (Aug. 25, 2020), pp. 73-80, XP093365490, ISSN: 2059-450X, DOI: 10.33590/emjreprohealth/20-00100 Retrieved from the Internet: URL:https://pmcncbi.nlm.nih.gov/articles/PMC7590498/pdf/nihms-1638999.pdf.
Wang Qian et al: "Smart Ultrasound Imaging and Perinatal, Preterm and Paediatric Image Analysis" First International Workshop, SUSI 2019, and 4th International Workshop, PIPPI 2019, Held in Conjunction with MICCAI 2019, Shenzhen, China, Oct. 13 and 17, 2019, Proceedings"", Jan. 1, 2019 (Jan. 1, 2001), Springer International Publishing, XP093365880, ISSN: 0302-9743, ISBN: 978-3-030-32875-7, vol. 11798, pp. 1-201, Retrieved from the Internet:.

* cited by examiner

ARTIFICIAL INTELLIGENCE SYSTEM FOR COMPREHENSIVE MEDICAL DIAGNOSIS, PROGNOSIS, AND TREATMENT OPTIMIZATION THROUGH MEDICAL IMAGING

CROSS-REFERENCE TO RELATED APPLICATIONS

This application is a Continuation-In-Part of U.S. patent application Ser. No. 17/573,246 filed on Jan. 11, 2022 which is a Continuation of U.S. patent application Ser. No. 17/352,290 filed Jun. 19, 2021, now U.S. Pat. No. 11,266,376, which claims the benefit of U.S. Provisional Patent Application No. 63/041,360 filed on Jun. 19, 2020; U.S. patent application Ser. No. 17/573,246 also is a Continuation of International Application PCT/US21/38164 filed on Jun. 20, 2021. This application also claims the benefit of U.S. Provisional Patent Application No. 63/451,844 filed Mar. 13, 2023. The disclosures of each of the aforementioned patent applications are incorporated herein by reference.

BACKGROUND OF THE INVENTION

Field of the Invention

The present invention relates to the field of medical imaging and artificial intelligence (AI). More specifically, it pertains to the integration of AI algorithms with ultrasound imaging for comprehensive medical diagnosis, prognosis, treatment, and monitoring. The invention encompasses a wide range of medical applications, including early detection and prediction of diseases, objective symptom measurement, treatment optimization, surgical planning, and real-time monitoring.

Description of the Prior Art

Ultrasound imaging is a well-established, non-invasive medical imaging modality that has been widely used for decades in various healthcare settings. It allows healthcare professionals to visualize internal body structures in real-time, without exposing patients to ionizing radiation. Ultrasound imaging has been particularly valuable in areas such as obstetrics, cardiology, and oncology, among others.

However, traditional ultrasound imaging relies heavily on the expertise of the operator for image acquisition and interpretation. This can lead to variability and subjectivity in diagnosis and treatment decisions, as well as a potential for missing subtle abnormalities or early signs of disease. Moreover, the vast amount of data generated by ultrasound imaging is often underutilized, as manual analysis can be time-consuming and may not fully capture complex patterns and anomalies.

In recent years, there has been a growing interest in applying AI techniques to medical imaging, including ultrasound. AI algorithms, such as machine learning and deep learning, have shown promise in automating image analysis tasks, detecting anomalies, and providing quantitative assessments.

However, existing AI-assisted ultrasound systems often focus on narrow, specific applications, such as detecting a single type of pathology or optimizing a particular aspect of the imaging process.

Furthermore, the development of AI-assisted ultrasound systems faces challenges in terms of data availability, quality, and diversity. Large, well-annotated datasets are essential for training accurate and robust AI models that can generalize across different patient populations and imaging conditions. However, the creation of such datasets is often hindered by privacy concerns, data sharing restrictions, and the need for manual expert annotation.

There is a need for a comprehensive AI-assisted ultrasound system that can address a wide range of medical applications, from early disease detection and prediction to treatment planning and monitoring. Such a system should be able to integrate state-of-the-art AI algorithms with ultrasound imaging, continuously learn and improve its performance by leveraging large, diverse datasets, and provide healthcare professionals with real-time insights and decision support.

The present invention addresses these limitations by proposing an AI-assisted ultrasound system that encompasses multiple medical domains and applications, while incorporating advanced AI techniques for improved accuracy, adaptability, and generalizability. By combining the power of AI with the non-invasive and widely accessible modality of ultrasound imaging, this invention aims to revolutionize the field of medical diagnosis, treatment, and monitoring, ultimately leading to improved patient outcomes and enhanced quality of care.

SUMMARY

Ultrasound imaging, and optionally other medical imaging techniques, are utilized to generate predictions and insights for comprehensive medical diagnosis, prognosis, and treatment optimization. These predictions involve analyzing various physiological conditions and biomarkers indicative of a wide range of health issues, offering an innovative method for early detection, proactive care planning, and personalized treatment strategies.

Various embodiments include using medical images or the raw data from which images can be produced, e.g., ultrasound images or raw ultrasound data, as inputs to a machine learning system configured to produce quantitative predictions and qualitative assessments regarding numerous medical conditions. These machine learning systems may leverage regression, classification approaches, and/or other algorithms suited for predictive analytics in healthcare. For instance, quantile regression or any suitable regression algorithm that outputs predictions in a range could be employed. In some embodiments, multiple algorithms are integrated within a single AI framework to enhance the predictive accuracy and reliability.

Preprocessing of images and/or pre-training of machine learning systems are also aspects of various embodiments. Preprocessing is particularly beneficial for dealing with medical images of poor quality, variable quality, or of different sizes, such as those commonly encountered with ultrasound imaging.

Various embodiments of the invention comprise a comprehensive medical diagnostic system designed to predict, diagnose, and monitor a wide range of health conditions, including: an image storage for retaining medical images showcasing relevant physiological conditions; image analysis logic for generating predictions and insights based on the medical images; a user interface for presenting these predictions to healthcare providers; and a microprocessor to facilitate the execution of image analysis logic. The image analysis logic optionally includes mechanisms for refining predictions based on specific indicators identified in ultrasound images. It will be appreciated that in various embodiments the image storage need nor store images, but can instead store raw data. Where raw data is used in place of images, instead of image analysis logic, analysis logic is employed.

The methodological aspects of the invention cover generating quantitative or qualitative predictions and assessments of various medical conditions. An exemplary method includes: acquiring a set of medical images or raw data; analyzing these images or raw data with a machine learning system to yield predictions and insights on health issues; and delivering these predictions to healthcare professionals for informed decision-making.

Training a medical determination system is another key methodological embodiment, involving: collecting a diverse range of medical images; optionally filtering these images for quality and relevance; optionally classifying images based on specific anatomical views or features; optionally pretraining a neural network to recognize distinct image features or types; training the neural network to make quantitative or qualitative predictions and assessments of medical conditions; and optionally evaluating the trained network's predictive performance. Such training can be performed analogously using raw data in place of images.

Acquiring medical images or raw data for neural network training encompasses: creating a comprehensive dataset of medical images or raw data; identifying images or raw data that are particularly indicative of physiological conditions relevant to various health issues; and using these images or raw data to fine-tune a neural network for accurate predictions and insights, enhancing early detection, prognosis, and treatment optimization strategies.

It will be appreciated that the AI-assisted methodologies described herein can be applied to a wide range of medical conditions and applications, including disease detection, drug use, allergy prediction, early disease diagnosis (diabetes, arthritis, IBD, etc.), pain and symptom measurement, drug selection and dosage optimization, clinical trial optimization, pregnancy and gynecological monitoring, abdominal, cardiovascular, renal, musculoskeletal, thyroid, testicular, breast, vascular, pulmonary, neurological, ophthalmic, skin, pediatric, digestive, respiratory, endocrine, lymphatic, joint, dental, metabolic, rheumatologic, hematologic, oncologic conditions, and continuous monitoring, such as with ultrasound patches.

Various embodiments of the invention are directed to a system configured to make a medical determination. In these embodiments the system comprises a storage storing images, or raw data, of body parts of a patient and/or a fetus, and analysis logic comprising a trained neural network in communication with the storage and configured to provide a prediction of an Apgar score at 1, 5 and 10 minutes after birth, based on the stored images or raw data. The systems of these embodiments further comprise a user interface configured to provide the determination to a user, and a microprocessor configured to execute at least the image analysis logic.

Additional embodiments are directed to a method for training a neural network to make a medical prediction. In these embodiments the method comprises a step of receiving a set of images, or raw data, of body parts of a plurality of patients and/or fetuses, where the images or raw data are tagged with Apgar scores at time of birth. The set of images, or the raw data, is then divided into a training set and a validation set, the images or raw data of the training set, and their tags, are provided to a neural network to train the neural network to predict Apgar scores based on the images or raw data of the training set. Then, images, or raw data, of a single patient from the validation set are provided to the neural network to make a determination of an Apgar score, and the determination is compared to the tag associated with the images or raw data.

Further embodiments are directed to a method for making a medical determination. In these embodiments the method comprises generating an image, or raw data, of a body part of a patient and/or a fetus, providing the image to a neural network that has been trained to predict an Apgar score from the image or raw data of the body part, and receiving the prediction of the Apgar score.

BRIEF DESCRIPTION OF DRA WINGS

DETAILED DESCRIPTION

The systems and methods disclosed herein offer either quantitative or qualitative assessments of a wide range of medical conditions. Here, a "quantitative determination" includes elements like probability assessments, classifications into various health-based categories, or estimates of disease progression at different time intervals. The advantage of quantitative determination lies in its capacity to provide considerably more actionable information compared to a mere qualitative classification.

Figure 1:
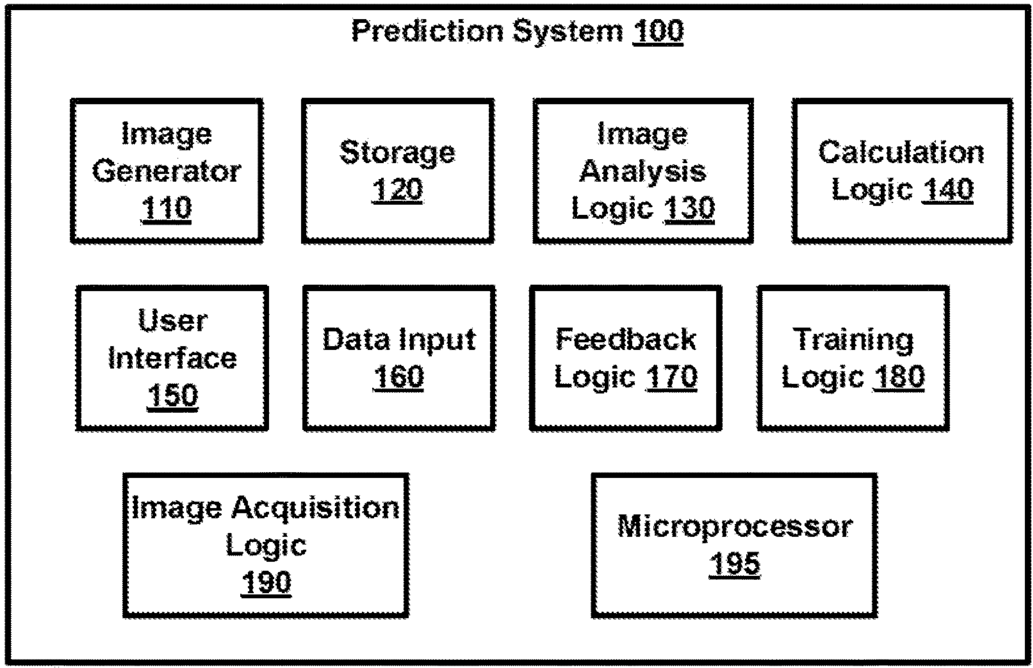
FIG. 1 illustrates comprehensive medical diagnostic systems designed to predict, diagnose, and monitor a wide range of health conditions using ultrasound and potentially other medical imaging techniques, according to various embodiments of the invention.

FIG. 1 depicts a Medical Determination System 100, tailored for comprehensive medical diagnosis, prognosis, and treatment optimization, in accordance with various embodiments of the invention. Determination System 100 may comprise multiple devices, including an ultrasound system and a computing device geared towards image processing. Optionally, the components of the Determination System 100 communicate with each other and with external devices through a communication network like the Internet.

Image or raw data processing, aimed at generating determinations, encompasses the generation of estimates pertaining to various medical conditions. These estimates can be presented as absolute or relative probabilities and may incorporate a temporal component. For instance, an estimate could signify a 66% likelihood that a patient will have an initially severe condition that will then likely improve with treatment.

Determination System 100 incorporates an optional Image Generator 110 responsible for producing medical images. Image Generator 110 may include a conventional ultrasound system or another imaging mechanism, configured to deliver images to other components within Determination System 100 for subsequent processing, such as via a computer network. In various embodiments, Image Generator 110 comprises a system that combines an image generation device with one or more elements of Determination System 100. For instance, Image Generator 110 can consist of an ultrasound device equipped with Storage 120, Image Analysis Logic 130, User Interface 150, and Feedback Logic 170, as discussed in greater detail elsewhere in this document. Image Generator 110 may also encompass diverse imaging technologies, such as radiographic (e.g., X-rays), magnetic resonance, nuclear, ultrasound, elastography, photoacoustic, tomography, echocardiography, magnetic particle imaging, spectroscopic (e.g., near-infrared), or similar devices and techniques. It should be noted that in this disclosure, references to ultrasound images are by way of example, and images from any of these other imaging techniques can be readily substituted for ultrasound images in these descriptions. In various embodiments the raw data produced by the Image Generator 110 can be used without having to first process that raw data into one or more images.

In some embodiments, various components of Determination System 100 are closely integrated with or housed within the Image Generator 110. To illustrate, consider Image Generator 110, which might encompass an ultrasound machine, housing Image Analysis Logic 130. This setup is adept at providing real-time feedback through Feedback Logic 170, effectively guiding the acquisition of ultrasound data and images.

In some embodiments, Image Generator 110 may include a sound source, a sound detector, and accompanying logic, all orchestrated to generate ultrasound images based on the sounds detected by the sensor. Image Generator 110 is designed to adapt the generation of these ultrasound images based on feedback received from Image Analysis Logic 130. A practical example of this adaptability involves fine-tuning the sound generation, focus, and processing parameters to enhance the detection of specific physiological conditions. Such adjustments respond to cues from Image Analysis Logic 130, which can signal that images or raw data containing such information would yield more accurate determinations and estimates.

It's important to note that Image Generator 110 becomes an optional component in scenarios where externally acquired images or raw data are fed into Determination System 100. In embodiments where raw ultrasound (sonogram) data is processed to generate medical assessments, Image Analysis Logic 130 obtains the raw data from the Image Generator 110 and the actual generation of images may be avoided. In some configurations, images and/or raw data are relayed to Determination System 100 via a communication network, such as the Internet. The imagery produced by Image Generator 110 could encompass a sequence illustrating the dynamic movements of various anatomical structures. This sequence, or the raw data behind it, can reveal details like blood flow patterns, tissue perfusion, heartbeat rhythm, and more. It can even incorporate Doppler information, providing insights into the direction and velocity of these movements.

Determination System 100 also includes Storage 120. This component contains digital memory capabilities for storing an array of data types or raw data types. Its storage capacity can accommodate raw sensor data, medical images, medical records, executable code (logic), neural networks, and other related data. For instance, it can house raw sensor data captured by a photon or acoustic detector, a dataset instrumental in generating images like X-rays or ultrasound scans. Storage 120, as discussed throughout this document, comprises memory circuits and data structures designed to manage and store the mentioned data categories. When dealing with ultrasound images, these images may optionally be configured at 600×600 pixels, optionally encompassing randomly selected crops of 400×400 pixels, which can be used in the training and determinations outlined herein. The term "ultrasound images" in this context may also encompass three-dimensional renderings created from ultrasound data.

In certain embodiments, Storage 120 is designed with circuits for the storage of raw data or ultrasound images acquired from patients. These can be collected in one or more separate acquisition sessions. For instance, during the first session, a sonographer might gather an initial set of ultrasound images, and subsequently, a second set of images may be procured in a subsequent session taking place at intervals of at least 1, 2, 5, 7, 15, 21, 30, 60, 90, or 365 days, or within any range between these durations. The raw data or ultrasound images for a particular patient may span over a duration encompassing any of the mentioned timeframes. In some instances, a patient could undergo weekly ultrasound sessions. These ultrasound images may encompass Doppler data and even sequences of images (e.g., videos), or the raw data thereof, illustrating the motion of various anatomical structures. Examples include images that reveal heartbeats or blood flow, and they may also incorporate data pertaining to the density of tissues, fluids, or bone. Images or raw data deemed valuable for making medical determinations encompass a broad spectrum, such as those depicting heart rate, liver condition, uterine status, intestinal health, skeletal structure, endometrial features (e.g., thickness and vascularization), kidney function, placental status, adnexa assessment, and so forth.

Determination System 100 further contains Image Analysis Logic 130. It is useful in providing either quantitative or qualitative predictions regarding various medical conditions, derived from the raw data or ultrasound images and optionally supplemented by clinical data. These predictions come in various formats. For instance, these predictions might incorporate estimates that encompass a wide array of patient-specific factors, such as potential co-morbidities.

In some embodiments, Image Analysis Logic 130 comprises multiple distinct logic components. Each logic component is designed to predict a specific aspect of a medical condition based on the raw data or ultrasound images. For example, one logic component could analyze ultrasound images to predict the severity of a condition, while another logic focuses on predicting the progression of the condition over time. These logic components can be housed within the same machine learning system for cohesive analysis.

Image Analysis Logic 130 exhibits adaptability when selecting machine learning algorithms for its calculations. For instance, in some embodiments, Image Analysis Logic 130 is configured to employ a regression algorithm, such as quantile regression, to furnish predictions of various aspects of a medical condition. These regression methods predict a range within which the actual answer is likely to fall, as opposed to a single point value. Any regression system capable of predicting ranges rather than specific values may be employed in Image Analysis Logic 130. This use of a range-based estimation helps to prevent overfitting of the data and proves valuable when the ultrasound images used for training may have mislabeled attributes. Image Analysis Logic 130 typically bases determinations and estimates on sets of ultrasound images or raw data, rather than relying on the analysis of a single ultrasound image or raw data suitable for constructing a single image.

In alternative embodiments, Image Analysis Logic 130 is programmed to predict various aspects of medical conditions based on classifications utilizing classification algorithms. These classifications can include categories such as "Mild," "Moderate," and "Severe," among others, depending on the specific condition being assessed. When classification algorithms are deployed, a "label smoothing" function may be applied. This smoothing function is particularly useful because certain training images or raw data may contain incorrect labels due to human error. The smoothing function may take a specific form, possibly involving epsilon (8) values of 0.05, 0.1, 0.3, or even greater.

Sample Label Smoothing:

Instead of using one-hot encoded vector, a noise distribution u(y|x) is introduced. The new ground truth label for data (xi, yi) becomes:

$$p'(y \mid x_i) = (1-\varepsilon)p(y \mid x_i) + \varepsilon u(y \mid x_i)$$

$$= \begin{cases} 1-\varepsilon+\varepsilon u(y \mid x_i) & \text{if } y = y_i \\ \varepsilon u(y \mid x_i) & \text{otherwise} \end{cases}$$

Where $\varepsilon$ is a weight factor, $\varepsilon \in [0, 1]$, and not that $\sum_{y=1}^{K} p'(y \mid x_i) = 1$.

This new ground truth label is used as a replacement for the one-hot encoded ground-truth label in a loss function.

$$L' = -\sum_{i=1}^{n}\sum_{y=1}^{K} p'(y \mid x_i) \log q_\theta(y \mid x_i)$$

$$= -\sum_{i=1}^{n}\sum_{y=1}^{K} [(1-\varepsilon)p(y \mid x_i) + \varepsilon u(y \mid x_i)] \log q_\theta(y \mid x_i).$$

Or, $$L' = \sum_{i=1}^{n}\left\{(1-\varepsilon)\left[-\sum_{y=1}^{K} p(y \mid x_i) \log q_\theta(y \mid x_i)\right] + \varepsilon\left[-\sum_{y=1}^{K} u(y \mid x_i) \log q_\theta(y \mid x_i)\right]\right\}$$

$$= \sum_{i=1}^{n}[(1-\varepsilon)\, H_i(p, q_\theta) + \varepsilon H_i(u, q_\theta)]$$

One can see that for each example in the training dataset, the loss contribution is a mixture of the cross entropy between the one-hot encoded distribution and the predicted distribution $H_i(p,q_\Theta)$, and the cross entropy between the noise distribution and the predicted distribution $H_i(u,q_\Theta)$. During training, if the model learns to predict the distribution confidently, $H_i(p,q_\Theta)$ will go close to zero, but $H_i(u,q_\Theta)$ will increase dramatically. Therefore, with label smoothing, one introduces a regularizer $H_i(u,q_\Theta)$ to prevent the model from predicting too confidently.

In some embodiments, label smoothing is used when the loss function is cross entropy, and the model applies the softmax function to the penultimate layer's logit vectors z to compute its output probabilities p. Label smoothing is a regularization technique for classification problems to prevent the model from predicting the labels too confidently during training and generalizing poorly. See, for example, https://leimao.github.io/blog/Label-Smoothing/.

In some embodiments, both a regression algorithm and a classification algorithm are used to predict various aspects of medical conditions. For example, Image Analysis Logic 130 can include two separate neural networks, one configured to apply the regression algorithm (that outputs a range) and the other configured to apply the classification algorithm. In this case, the classification algorithm may be applied before the regression algorithm and the regression algorithm is optionally applied separately to each class.

Alternatively, both the regression algorithm and the classification algorithm may be applied by the same neural network. In such embodiments, the neural network is trained to produce both a classification and a regression-based prediction, both of which are quantitative. A regression algorithm outputs one or more values for each percentile chosen. For example, some embodiments use 10%, 25%, 50%, 75%, and 90% percentiles for outputs (which represent percentiles of a quantitative prediction), and each of these percentiles may be associated with a probability and/or a confidence measure. From a set of image inputs or corresponding raw data, the neural network of Image Analysis Logic 130 typically generates one or more values for each percentile chosen. Multiple outputs from distinct algorithms may be used to confirm a prediction of a set of medical condition parameters. This scenario is optionally used to establish confidence in the overall prediction since the regression and classification algorithms should produce the same result.

Image Analysis Logic 130 may employ other machine learning algorithms or combinations thereof, in addition to or as an alternative to regression and classification. For example, Image Analysis Logic 130 may be configured to apply a regression that outputs an estimated range, a range being more accurate and/or useful than single point predictions. However, single point predictions can be used if many neural networks are generated (each trained on a different subset of the images/raw data) from different subsets of the data, which are then statistically analyzed to form an average and/or distribution. In some embodiments, a Bayesian neural network is used to capture the epistemic uncertainty, which is the uncertainty about the model fitness due to limited training data. Specifically, instead of learning specific weight (and bias) values in the neural network, the Bayesian approach learns weight distributions, from which it samples to produce an output for a given input, to encode weight uncertainty. Bayesian networks can also be used in a similar fashion in the classification approaches to prediction discussed herein.

As previously highlighted, Image Analysis Logic 130 can be configured, employing the aforementioned algorithmic and machine learning techniques, to predict various aspects of medical conditions. These predictions are grounded in the comprehensive analysis of ultrasound images or raw data, potentially complemented by additional patient-related factors. For instance, Image Analysis Logic 130 may be tailored to derive the aforementioned evaluations from clinical data. This clinical dataset can encompass a range of variables, such as genetics, body weight, patient medical history, blood glucose levels, heart functionality, kidney performance, blood pressure readings, infection status, nutritional profiles, substance use (including smoking and alcohol consumption habits), patient age, socioeconomic status, living environment, income levels, and even ancestral background. Image Analysis Logic 130 can be strategically configured to accept any singular element from this clinical dataset or combine multiple factors to generate the predictions discussed herein, partly predicated on this clinical information.

Optionally, Determination System 100 integrates Calculation Logic 140, designed to derive outputs based on the predictions generated by Image Analysis Logic 130. For instance, Calculation Logic 140 can be programmed to compute the severity of a condition, alongside an estimate of its progression over time. Calculation Logic 140 may achieve this by calculating a prediction through the utilization of a probability distribution, represented, for instance, in percentiles. Furthermore, Calculation Logic 140 can ascertain the probability of a particular set of outcomes by employing a distribution function on the estimates provided by Image Analysis Logic 130 and subsequently generating a probability distribution based on this data. In certain embodiments, Image Analysis Logic 130 is equipped to generate specific characteristics associated with this distribution function. For example, in select instances, an estimation of prediction reliability can be factored into the determination, allowing for the calculation of a width parameter (e.g., standard deviation) of the distribution function. It's important to note that Calculation Logic 140 may be integrated within Image Analysis Logic 130, offering an alternative approach to processing and analysis.

Determination System 100 optionally further includes a User Interface 150 configured to provide to a user estimates and/or determinations made using Image Analysis Logic 130. User Interface 150 optionally includes a graphical user interface (and the logic associated therewith) and may be displayed on an instance of Image Generator 110, a mobile device (in which case User Interface 150 can include a mobile app) or on a computing device remote from Image Generator 110 and/or Image Analysis Logic 130. For example, User Interface 150 may be configured to display predictions and insights related to various medical conditions. In some embodiments, User Interface 150 is configured for a remote user to upload one or more ultrasound images or raw data for processing by Image Analysis Logic 130.

As is discussed further herein, in some embodiments, User Interface 150 is configured to provide feedback to a user in real-time. For example, User Interface 150 may be used to give instructions to an ultrasound technician during an ultrasound session, to generate raw data or images which result in a better prediction of a medical condition.

Determination System 100 optionally further includes a Data Input 160 configured to receive data regarding a patient, e.g., clinical data regarding the patient. Data Input 160 is optionally configured to receive any of the clinical data discussed herein, which may be used by Image Analysis Logic 130 to generate the estimates and/or probabilities discussed herein. For example, this data can include any of the clinical data discussed herein, or inputs from a user of Image Generator 110. In some embodiments, Data Input 160 is configured to receive medical images, such as ultrasound images, or receive the corresponding raw data, from remote sources.

Determination System 100 optionally further includes Feedback Logic 170. Feedback Logic 170 is configured to guide acquisition of ultrasound images or raw data based on a quality of the estimate and/or determinations related to the patient. For example, if analysis of ultrasound images, using Image Analysis Logic 130, obtained during an imaging session, results in determinations and/or estimates having inadequate precision, accuracy, and/or reliability, then Feedback Logic 170 may use User Interface 150 to inform a user that additional ultrasound raw data or images are desirable.

Further, in some embodiments, feedback logic is configured to direct a user to obtain ultrasound raw data or images of specific features such as motion of a heartbeat, heart rate, the liver, the kidneys, blood flow, bone development, spine, tissue perfusion, uterus, ovaries, testicles, femur, humerus, endometrium, endometrium vascularization, the adnexa, and/or the like. In some embodiments, Image Analysis Logic 130 is configured to classify ultrasound raw data or images according to subject matter and/or objects included within the images or raw data. For example, separate subject matter classes may include any of the views and/or features discussed herein. In such embodiments, Image Analysis Logic 130 may be configured to identify objects in the ultrasound images or raw data and determine that there are sufficient quality images or data of objects in each subject matter classification. (Subject matter classification is not to be confused with classification of ultrasound images relating to medical conditions.) If there are not sufficient raw data or images, then the User Interface 150 may be used to request that the operator of Image Generator 110 obtain additional images or raw data including the additional objects. Feedback Logic 170, thus, may be configured to indicate a need to acquire additional ultrasound images or raw data useful in the prediction of various medical conditions. In a specific example, Image Analysis Logic 130 may be configured to request at least one set of images indicative of a specific condition. In some instances, Feedback Logic 170 is configured to guide the positioning of the image generator (e.g., an ultrasound head) so as to generate images or raw data that are more useful in the prediction of medical conditions. Such guidance may include positioning of an ultrasound probe in a specific position or a written/audio request such as "obtain images showing the liver."

In various embodiments, Feedback Logic 170 is configured to guide or request acquisition of new images or raw data that would be beneficial to training future models to obtain greater accuracy.

Determination System 100 optionally further includes Training Logic 180. Training Logic 180 is configured for training Image Analysis Logic 130, Feedback Logic 170, Image Acquisition Logic 190, and/or any other machine learning system discussed herein. Such training is typically directed at the end goal of learning to make quantitative determinations and/or estimates relating to various medical conditions. For example, Training Logic 180 may be configured to train Image Analysis Logic 130 to make a quantitative prediction of the severity of a condition. As described elsewhere herein, this determination may be made using both a quantile regression algorithm and a classification algorithm, together or separately.

While Training Logic 180 may use any applicable selections of the commonly known neural network training algorithms, Training Logic 180 optionally includes a variety of improvements to better train the neural networks disclosed herein. For example, in some embodiments Training Logic 180 is configured to pretrain a neural network of Image Analysis Logic 130 to better recognize features in ultrasound images or raw data. This pretraining can include training on images with varying orientation, contrast, resolution, point of view, etc., and can be directed at recognizing anatomical features within the ultrasound images. Pretraining is optionally performed using unlabeled data.

In some embodiments, Training Logic 180 is configured to generate additional training images or raw data, in cases where training images or raw data for a specific condition are sparse or infrequent. For example, once it is known which images and features are most predictive, Training Logic 180 can take subsets of the images, and use a GAN (Generative Adversarial Network) to generate new training images including the features found in rare clinical situations.

In some embodiments, Training Logic 180 is configured to train on multiple sets of images or corresponding raw data, the images optionally being from different patients. By training on multiple sets of images, rather than on single images, overfitting of the data can be reduced. Preferably, each of the sets is large enough to assure that there are at least some images, or corresponding raw data within the set including information useful for making the predictions discussed herein.

In some embodiments, Training Logic 180 is configured to train Image Analysis Logic 130 to enhance images. For example, Image Analysis Logic 130 may be pretrained to enhance poor quality ultrasound images, or to reveal features, such as tissue perfusion and/or vascularization, that would not normally be visible in the ultrasound images being processed. Such enhancement may allow the use of a handheld ultrasound image to generate the images processed to make predictions of various medical conditions.

In some embodiments, Training Logic 180 is configured to train neural networks in multiple stages, e.g., as in transfer learning. For example, a neural network may first be trained to recognize relevant patient features, then be trained to predict categories of medical conditions, and then be trained to provide a quantitative prediction of the severity or progression of those conditions.

Determination System 100 typically further includes a Microprocessor 195 configured to execute some or all of the logic described herein. For example, Microprocessor 195 may be configured to execute parts of Image Analysis Logic 130, Calculation Logic 140, Feedback Logic 170, Training Logic 180, and/or Image Acquisition Logic 190. Microprocessor 195 may include circuits and/or optical components configured to perform these functions.

Figure 2:
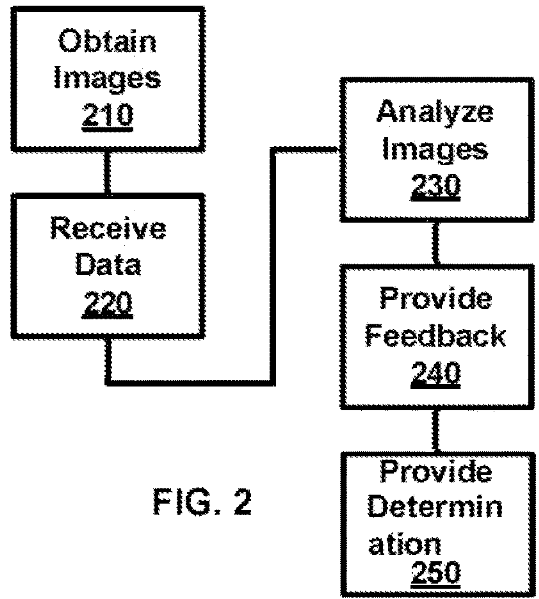
FIG. 2 illustrates methods of generating predictive assessments and insights for various medical conditions through the analysis of medical imaging data, according to various embodiments of the invention.

FIG. 2 illustrates methods of making a quantitative (optionally medical) prediction, according to various embodiments of the invention.

In an Obtain Images Step 210, a set of one or more images, or corresponding raw data, are obtained. These images or data are typically related to a specific patient. These images or data may be obtained from a source external to Determination System 100 or may be obtained using Image Generator 110. For example, in some embodiments, ultrasound images are uploaded to Storage 120 via a computer network such as the internet. Images may be received from an electronic medical records system. In other embodiments, images are generated using a medical imaging system such as any of those discussed herein. The images or raw data are optionally stored in Storage 120. The images can include any combination of the views and/or features discussed herein and are optionally classified based on their respective views and features (subject matter classification).

In an optional Receive Data Step 220, additional clinical data regarding the patient is received. Again, this data may be received from an electronic medical records system, provided by the patient, and/or provided by a caregiver. The received clinical data can include any of the clinical data discussed herein and is optionally received via Data Input 160.

In an Analyze Images Step 230 the images or raw data obtained in Obtain Images Step 210 are analyzed using Image Analysis Logic 130. The images or data are analyzed to produce one or more quantitative or qualitative predictions. For example, a quantitative prediction can include an estimate of the severity or progression of a medical condition. The determination is a "quantitative determination" as defined elsewhere herein. In addition to the images or raw data, the quantitative prediction is optionally further based on the clinical data received in Receive Data Step 220. The methods of analysis in Analyze Images Step 230 can include any combination of the algorithms and/or machine learning systems discussed elsewhere herein, including those discussed with reference to Image Analysis Logic 130. For example, analyzing medical images can include using a quantile regression algorithm and/or a classification algorithm to make a quantitative determination relating to a medical condition. In another example, analyzing the medical images includes using a regression algorithm to provide a prediction of the severity or progression of a condition.

In an optional Provide Feedback Step 240, a user (e.g., a caregiver, or possibly the patient) is provided with feedback regarding acquisition of the images or raw data. This feedback can be based on, for example, a quality of the quantitative determination and/or a classification of images or data already acquired. In specific examples, during an ultrasound session, a caregiver may be asked to acquire additional images of different resolution, of different views, of different features, and/or the like. Obtain Images Step 210 and Analyze Images Step 230 are optionally repeated following Provide Feedback Step 240.

In a Provide Determination Step 250 the quantitative or qualitative determination(s) generated in Analyze Images Step 230 is provided to a user, e.g., a patient or caregiver. The predictions are optionally also placed in Storage 120 and/or an electronic medical records (EMR) system. In various embodiments, the predictions are provided via a web interface, via the EMR system, via a mobile application, on a display of Image Generator 110, on a display of a computing device, and/or the like.

Figure 3:
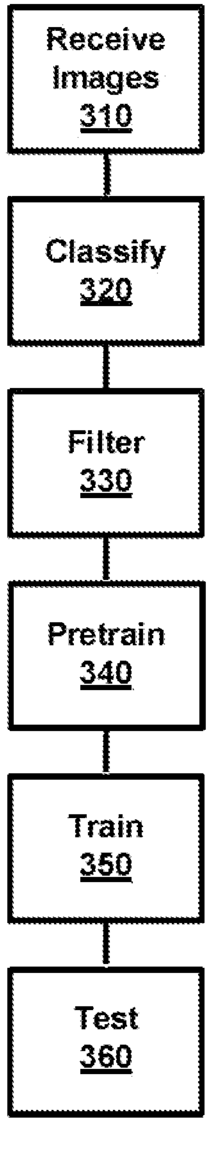
FIG. 3 illustrates methods of training a comprehensive medical diagnostic system to accurately predict, diagnose, and monitor health issues based on physiological conditions discernable in raw data or visible in ultrasound images, according to various embodiments of the invention.

FIG. 3 illustrates methods of training a medical prediction system, according to various embodiments of the invention. The methods illustrated by FIG. 3 are optionally used to train Image Analysis Logic 130, Feedback Logic 170, and/or Image Acquisition Logic 190. The methods may be performed using Training Logic 180.

In a Receive Images Step 310, a plurality of medical images or corresponding raw data are received as a training set. The received medical images optionally include ultrasound images or raw data of a patient before or after an intervention to establish the effect on the prediction of various medical conditions. The received images or data are optionally stored in Storage 120.

In an optional Classify Step 320, the received images or raw data are classified according to the views or features included within the images. For example, an image may be classified as showing the heart or classified as showing the liver. Classify Step 320 is optionally performed by a neural network included in Image Analysis Logic 130 and/or trained by Training Logic 180. Classify Step 320 may also include classifying images or raw data according to (actual or estimated) the various anatomy that may have differing impacts in a particular medical condition prediction. For example, images may be classified as having been generated during a follow up of specific anatomy. It should be noted that as used herein, "neural network" specifically excludes human brains.

In an optional Filter Step 330, the received images or raw data are filtered. Filtering can include removing images that lack features or views that have been determined to have little or no determinative value. For example, a class of images of a bladder may be determined to have little value in determining a quantitative or qualitative determination, and this class of images may be removed from the training set. Images or raw data may also be filtered according to their quality or resolution, etc.

In some embodiments, Filter Step 330 includes balancing of a number of images or raw data in various classes. For example, for training purposes, it may be desirable to have roughly equal numbers of rare medical conditions, unusual clinical circumstances, or uncommon hardware. Specifically, balancing may be used to adjust quantities of the images or raw data based on ground truth medical diagnoses. Likewise, for training purposes, it may be desirable to balance numbers of images within the training set based on classification of views and/or features as determined in Classify Step 320.

In an optional Pretrain Step 340, the neural network is optionally pretrained to recognize features within the images or types of images. For example, a neural network within Image Analysis Logic 130 may be pretrained to recognize features in ultrasound images of varying orientation, resolution, and/or quality.

In a Train Step 350, the neural network is trained to provide a quantitative or qualitative determination regarding predicted medical conditions.

In an optional Test Step 360, predictions made by the neural network trained in Train Step 350 are tested using test images or raw data. This testing may be performed to determine the accuracy and/or precision of the quantitative or qualitative determinations generated by the neural network.

The quantitative or qualitative predictions of medical conditions are optionally used to selectively select a population for a clinical trial. For example, assuming that a certain rare condition occurs in less than 1% of patients, it would be inefficient to give a general population of patients a candidate therapy in order to detect a benefit to the unidentified 1% of patients. However, by identifying the 1% of the patients most likely to develop this condition, a study can be made of the benefit seen within this population for a candidate therapy. Such a study is much more efficient and more likely to reveal benefits with better statistical relevance. The systems and methods disclosed herein may be used to identify such preferred populations for clinical studies. This approach is particularly beneficial for conditions that begin development (and could benefit from therapy) well before clear symptoms appear.

The various methods illustrated in FIGS. 2 and 3 are optionally used in combination and are optionally performed using the systems illustrated by FIG. 1. For example, the methods of FIGS. 2 and 3 may be used together.

It should be understood that the present invention is not limited to only the prediction of specific medical conditions; methods described herein can be used for identifying a wide range of diseases and medical conditions that may happen in the future. Those of ordinary skill will be able to identify still other conditions that AI can be trained to determine future medical events or conditions.

Example

The following is an illustrative example, which may be included in any of the embodiments discussed herein:

All ultrasounds from any patient are used to train the neural networks discussed herein. However, different models can be created for predicting Apgar scores at different time intervals.

Note: The following models are simply individual embodiments that show how to create a working model. Many of the hyperparameters such as the learning rate, batch size, and number of epochs can be adjusted without issue.

A machine learning algorithm (the code), set forth below, was created and used to train a neural network to make predictions of Apgar scores at 1, 5, and 10 minutes after birth, based on ultrasound images acquired from the patient. Both transformer and CNN architectures were successfully used. The training was conducted using a dataset of ultrasound images, totaling 276,577 images labeled with the Apgar score at time of birth. The dataset representing 14,302 individual ultrasound sessions. The images were acquired of female reproductive anatomy and fetal anatomy. The dataset was split into a training set and a validation set. Ten percent of the studies were selected randomly to comprise the validation set, the remaining images comprised the training set. Next, using the labeled data in the training set, the algorithm gradually learned to extract relevant features from these images, such as anatomical structures that may be different depending on different Apgar scores, but not necessarily visible to the human eye. For Apgar scores, the relevant anatomical structures were found to be primarily the fetal anatomy for normal deliveries and the anatomy of the mother in cases where the Apgar score is driven primarily by a preterm birth situation. During the training session the algorithm was repeatedly tested against the validation set which does not participate in the training. The algorithm's performance was evaluated on the validation set of ultrasound images that had not been used for training, and the algorithm's predictions were compared against the actual labels. The training was halted once the validation accuracy began to decrease after reaching a peak accuracy, indicating the algorithm was likely no longer learning generalized features, but more likely memorizing features of the training set. The algorithm proved accurate on the validation data, yielding an accuracy of 85%.

Import all the libraries used in the code

```
from fastai.vision.all import*
```

Any imaging study where the Apgar score was between 0-3 can be labeled "Low", and "Moderately Abnormal" for 4-6, and "Reassuring" for 7-10. However, this labeling is not strictly necessary; other classification labels may be used.

The following path is a folder containing one subfolder for each class to be predicted which are "Low", "Moderately Abnormal", and "Reassuring". This is only one embodiment; any number of different classifications would also work. For example, there may be two, three, four or more classes. For example "No Response to Stimuli" could be added.

A score of Low is about 5% of the total dataset used, however training may be more effective when using a balanced dataset which is the case here. The validation set is not balanced in this embodiment which reflects the accuracy of the distribution in the real world, but could be balanced in other embodiments. In some embodiments the neural network has an equal chance of being fed an instance of one of the categories. In various embodiments, at least 50% or 75% of the training set includes images balanced among the possible classes.

A large dataset containing over 276,577 million ultrasound images with annotations about the Apgar scores was used for the training and validation of this invention. Optionally, the image size can be set to 400 by 400 pixels. Most of the images in this dataset are several times this size and are reduced in size for training and inference efficiency. Accuracy can increase with increasing image size, however there can be diminishing returns. Alternative embodiments use images of at least 224×224 pixels, 640×640 pixels, or 2048×2048 pixels, or any range therebetween.

This will create an object to feed data to the neural network during training and validation. In this example, 10% of the studies are put into a validation set which is used to monitor training. The validation set contains the same distribution of Apgar scores that exists in the original dataset. The data is balanced for training; however, the validation set is the natural distribution and not balanced in any way. The batch size is arbitrarily set to 48 images but can be adjusted if necessary. Adding the function aug_transforms causes each image to be randomly augmented which can reduce overfitting. Examples of augmentation include but are not limited to adjusting brightness, contrast, and flipping the image horizontally. This embodiment uses Cross Entropy as the loss function and it is training as a label classification problem where there is exactly one label for each image. Other embodiments could use other loss functions such as mean squared error if the data is viewed as a regression problem.

```
from fastai.vision.all import
# Define data transformations
tfms = aug_transforms( )
image_size = 400
# Get image file names from the specified path
names = get_image_files(path)
# Create a DataBlock for label classification
dblock = DataBlock(
  blocks=(ImageBlock, CategoryBlock),
  get_items=get_image_files,
  get_y=Pipeline([parent_label]),
  splitter=GrandparentSplitter( ),
  item_tfms=Resize(image_size),
  batch_tfms=[*tfms])
# Create DataLoader
dls = dblock.dataloaders(path, bs=48)
```

Create an object which will control training and inference at a high level. Using a high value for weight decay is one example. Other forms of regularization of the weight values may have similar effects.

Obtain a pretrained network for use in transfer learning, however training a neural network from an initial randomized form will also work. In this case ResNet-152 is used. Other variations of resnet will work and the more layers the better the accuracy. Many other neural networks will also give usable results. The example below illustrates an example of training. The parameters and steps may be varied in alternative embodiments.

Create a learner object with a CNN architecture (however vision transformers may also be used)

```
learn = cnn_learner(dls,
  resnet152,
  cbs=[ShowGraphCallback( )],
  wd=0.1,
  metrics=[accuracy],
  loss_func-CrossEntropy WithLogitsLossFlat( ))
```

This will freeze the parameters of the convolutional part of the neural network and will allow training of just the linear layers. Other embodiments will not necessarily require the step of freezing layers.

```
learn.freeze( )
```

Train the neural network for 10 epochs while gradually increasing then decreasing the learning rate with a scheduler. The maximum learning rate will be 1e-3. Other embodiments may use an alternative training schedule.

```
learn.fit_one_cycle(10, le-3)
```

This will allow the entire neural network to be trained including the convolutional layers.

learn.unfreeze( )

Further train the neural network for 5 epochs while gradually increasing then decreasing the learning rate with a scheduler. The maximum learning rate will be 1e-5.

```
learn.fit_one_cycle(5, le-5)
```

Further train the neural network for 5 epochs while gradually increasing then decreasing the learning rate with a scheduler. The maximum learning rate will be 1e-5.

```
learn.fit_one_cycle(5, le-5)
```

Best validation accuracy of this embodiment is 85%.

This network allows for the identification of the specific anatomical views of the study that are most useful for making this prediction. Specific anatomical views or any other information fed to the network can be excluded if it is commonly uninformative, or the various views can be weighted in calculating the final determination.

Each determination outputs a score of how confident the model is which can be used in real time on the ultrasound machine to inform the ultrasound technician when a view which will improve accuracy has been obtained, or the software can automatically capture high confidence views as they are found with no effort from the technician required. This technique can be used to create training sets for continuous improvements in updated models which is a feedback loop for capturing better data for training future models.

The trained system is optionally used to provide an ultrasound technician with real-time feedback. For example, the system may inform the technician when images expected to be the most predictive have or have not been obtained. The system can request that the technician obtain images or raw data of specific anatomy of the patient and/or fetus. When an obtained image or raw data is identified as being predictive of the Apgar score, the system may request that the technician obtain additional images or raw data to confirm or negate the prediction. For example, if an image of one part of the anatomy (e.g., a heart) confidently predicts an Apgar score the system may request that the technician obtain further images of that anatomy or further images of another part of the patient's anatomy (e.g., cervix or uterus).

Making determinations based on individual ultrasounds and then aggregating these individual determinations can be useful in itself, but the method can also be improved upon. One concern with this method is that within a single ultrasound recording session some ultrasound images or data may predict one Apgar score while ultrasound images or raw data of another part of the anatomy will predict a different Apgar score, making a simple aggregation less effective. Accordingly, neural networks have been created that allow multiple images or corresponding raw data to be classified in a single pass through a neural network or sequence of networks. As the number of images or quantity of raw data simultaneously fed into a neural network increases, the accuracy also typically increases. Therefore, more efficient methods of passing (in parallel, or sequentially) multiple images or data through a single network (or sequence of networks) were developed.

This does not necessarily have to be a classification problem. The values to determine could be numeric values representing the desired target and a neural network to perform a regression is created instead.

Training data can be created by training a neural network to modify images or raw data from one class into another if the data is limited for a particular class. An example of a neural network which can convert images from one class to another is a cyclegan.

As provided above, it is not necessary for images to be used. The underlying raw data in the form of sound waves captured by the ultrasound machine before conversion into an image can also be used as an alternative to or in addition to images for this determination.

Transformer Aggregation Architecture

A neural network can be created which can extract the useful information from each image or corresponding raw data which is then aggregated using multiple neural networks combined into a single neural network using a transformer style architecture, however these networks could be separate in other embodiments. An ultrasound session is one in which a technician takes a set of images or raw data in one interaction with a patient. Considering that many ultrasound sessions exceed 100 images, this is useful for processing efficiency and accuracy. Transformers can be applied to sequential (or time series) data where data points are correlated in a sequence. The ultrasound images or raw data in an ultrasound session don't have a significant amount of order to them, if any, however this type of network can carry information from a previous step of processing a single image forward and this combined information can be classified after each image in an ultrasound session is processed. Ultrasound sessions do not have a significant amount of order because an ultrasound technician typically jumps from viewing one anatomical feature to another anatomical feature. It is possible to record a video of the entire session and in these embodiments the images in the video have a sequential nature and this general technique can be employed.

```
from fastai2.vision.all import *
from pathlib import Path
```

Get the data which is divided into training, validation, and test sets. The training data is created in an unusual way. Instead of just using each study as a separate folder of images, folders are created which randomly sample a range of images from pools of all studies with the same Apgar score. It is also possible to sample images from a pool of each class of the desired sequence length at run time. Other embodiments use 2, 3 or more classes or numeric values. There is one main reason to do this.

The training data can contain a significant number of mislabeled studies. By taking a random selection it makes it possible for each training sample to have some ultrasounds which contain the needed information to make a correct determination and to prevent overfitting of incorrectly labeled studies.

It should also be noted that multiple ultrasound sessions are commonly performed on a single pregnancy. Multiple sessions from a single pregnancy could also be combined when performing a prediction of Apgar scores.

A single session may indicate a predicted low Apgar score but may not have a high confidence. Therefore, the system may indicate that a follow up session is desired and potentially when the follow up session should be conducted.

Data Acquisition

To obtain the paths to folders containing images from individual studies, the following function can be used:

```
def get_sequence_paths(path):
  sequence_paths = [ ]
  for folder in path.ls( ):
    for c in folder.ls( ):
      sequence_paths += c.ls( )
  return sequence_paths
folders = get_sequence_paths(IMAGES_PATH)
```

In this example, the sequence length is set to 36 images, but a smaller or larger range can be used. More images may improve results, but there can be diminishing returns. The image size used here is 400×400 pixels, which is larger than the typical 224×224 pixels used in image classification problems. However, smaller or larger images can also be utilized:

```
seq_len = 36
image_size = 400
```

A custom ImageTuple class is defined to handle image sequences and display them:

class ImageTuple(Tuple):

```
def show(self, ctx=None, ** kwargs):
  n = len(self)
img0, img1, img2 = self[0], self[n//2], self[n-2]
if not isinstance(img1, Tensor):
  t0, t1, t2 = tensor(img0), tensor(img1), tensor(img2)
  t0, t1, t2 = t0.permute(2, 0, 1), t1.permute(2, 0, 1), t2.permute(2, 0, 1)
else:
  t0, t1, t2 = img0, img1, img2
return show_image(torch.cat([t0, t1, t2], dim=2), ctx=ctx, ** kwargs)
```

An Image Tuple Transform is also created to encode images into tuples for our dataset:

class Image Tuple Transform(Transform):

```
  def_init_(self, seq_len=36):
    self.seq_len = seq_len
  def encodes(self, path):
    images = path.ls( )
    return ImageTuple(tuple(PILImage.create(f) for f in L(random.choices(list(images),
k=self.seq_len)) if os.path.isfile(f)))
tfms = aug_transforms(flip_vert=False)
grandparent_splitter = GrandparentSplitter( )(files)
itfm = Image Tuple Transform(seq_len=seq_len)
ds = Datasets(files, tfms=[itfm], [parent_label, Categorize]], splits=grandparent_splitter)
```

-continued

```
dls = ds.dataloaders(bs=bs, after_item=[Resize(image_size), ToTensor], after_batch=
[*tfms,
IntToFloatTensor], drop_last=True)
Encoder Class
```

The Encoder class loads a model pretrained on single ultrasound images, removes the final classification layer, and returns 512 features for each image:

```
class Encoder(Module):
  def __init__(self, **kwargs):
    model = load_learner("resnet152_base_model").model
    self.body = model[0]
    self.head = model[1][:-4]
```

-continued

```
  def forward(self, x):
    return self.head(self.body(x))
```

This class allows features to be extracted from images using a pretrained model. The number of features can be adjusted as needed for specific use cases.

The following module takes the features from each image and classifies the entire sequence of images.

```
import torch
import torch.nn as nn
import torch.nn.functional as F
class TransformerEncoder(Module):
  def_init_(self, num_classes=2, d_model=512, nhead=8, num_encoder_layers=6,
dim_feedforward=2048, dropout=0.1):
    self.transformer_encoder = nn. TransformerEncoder(
      nn. TransformerEncoderLayer(d_model, nhead, dim_feedforward, dropout),
      num_encoder_layers
    )
    self.fc = nn.Sequential(
nn.Linear(d_model, num_classes),
    )
  def forward(self, x):
    x = self.transformer_encoder(x)
    x=x.mean(dim=1) # Pooling operation, you can replace this
with another method if needed
    x = self.fc(x)
    return x
Example usage:
dls_c = 2
model = TransformerEncoder(num_classes=dls_c, d_model=512, nhead=8,
num_encoder_layers=6, dim_feedforward=2048, dropout=0.1)
```

Create a Learner object which will control training and inference at a high level. Using a high value for weight decay is helpful in making a correct determination.

GradientAccumulation can be used if GPU memory constraints require it. This will accumulate gradients for 32 items before making an update to the weights of the network.

```
import torch.nn as nn
from fastai.learner import cnn_learner, Learner
from fastai.vision.all import ShowGraphCallback, GradientAccumulation, SaveModelCallback
class TransformerModel(nn.Module):
  def_init_(self, num_classes, d_model=512, nhead=8, num_encoder_layers=6,
dim_feedforward=2048, dropout=0.1):
    # transformer architecture here
  def forward(self, x):
    # Forward pass through the transformer
# Custom splitter function to separate transformer encoder from other layers
def transformer_splitter(model):
  transformer_layers = [ ]
  other_layers = [ ]
  for name, param in model.named_parameters( ):
    if 'transformer_encoder' in name:
      transformer_layers.append(param)
    else:
      other_layers.append(param)
  return [transformer_layers, other_layers]
# Create your data loaders (dls) here
# Replace 'dls' with the actual data loaders
# Instantiate your TransformerModel
```

-continued

```
model = TransformerModel(num_classes=dls.c)
# Create a Learner with the model and custom splitter
learn = Learner(dls,
          model,
          wd=0.3,
          metrics=[accuracy],
          cbs=[ShowGraphCallback( ), GradientAccumulation( ),
SaveModelCallback(monitor='valid_loss', fname='Transformer_Model')],
          splitter=transformer_splitter).to_fp16( )
```

Train the neural network for 5 epochs while gradually increasing then decreasing the learning rate with a scheduler. The maximum learning rate will be 1e-3. These parameters are simply chosen for this embodiment, many other choices would also work.

```
learn. freeze( ) learn.fit_one_cycle(5, le-3)
```

Alternative Embodiments

To aggregate the individual determinations for a study run each through a tournament to determine final classification.

Reinforcement learning can be used in place of the transformer shown.

Use multiple models trained on different subsets of the data to create ensembles which typically increases accuracy.

Use additional data about the patient in combination with the images or raw data such as age or relevant events in the medical history of a patient.

Additional outputs in addition to the predicted medical condition can be used. Some examples are age, comorbidities, sex, among others. Having multiple outputs for determination can improve the overall accuracy of the determination due to the inherent relationships between the various items being determined. Any of these alternative determinations can be performed without the primary condition prediction if desired.

The systems and methods disclosed herein have been applied to real world data obtained from a clinical context and have been shown to consistently produce an accuracy of at least 85% for predicting various medical conditions.

Several embodiments are specifically illustrated and/or described herein. However, it will be appreciated that modifications and variations are covered by the above teachings and within the scope of the appended claims without departing from the spirit and intended scope thereof. For example, while ultrasound images and raw ultrasound data are taught herein by way of example, the systems and methods described herein may be applied to other medical imaging modalities and conditions. Examples include disease detection, drug use, allergy prediction, early disease diagnosis (diabetes, arthritis, IBD, etc.), pain and symptom measurement, drug selection and dosage optimization, clinical trial optimization, pregnancy and gynecological monitoring, abdominal, cardiovascular, renal, musculoskeletal, thyroid, testicular, breast, vascular, pulmonary, neurological, ophthalmic, skin, pediatric, digestive, respiratory, endocrine, lymphatic, joint, dental, metabolic, rheumatologic, hematologic, oncologic conditions, and/or any other medical condition the precursors of which may be present in a medical image or the underlying raw data. The methods and systems disclosed may be used to determine a current clinical state separately or in combination with the (optionally quantitative or qualitative) determination of a future state. The systems and methods disclosed herein may also be used to predict future health conditions of a patient. For example, the aforementioned conditions and applications could be predicted. It will be understood that the terms "predict" and "determine" are used interchangeably herein.

While the teachings herein include use of medical images, e.g., ultrasound images, in various embodiments, the systems and methods may use raw data other than in the form of images. For example, Image Analysis Logic 130 is optionally trained to process raw ultrasound data rather than or in addition to images generated from such data.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

The "logic" discussed herein is explicitly defined to include hardware, firmware or software stored on a non-transient computer readable medium, or any combinations thereof. This logic may be implemented in an electronic and/or digital device to produce a special purpose computing system. Any of the systems discussed herein optionally include a microprocessor, including electronic and/or optical circuits, configured to execute any combination of the logic discussed herein. The methods discussed herein optionally include execution of the logic by said microprocessor.

Computing systems and/or logic referred to herein can comprise an integrated circuit, a microprocessor, a personal computer, a server, a distributed computing system, a communication device, a network device, or the like, and various combinations of the same. A computing system or logic may also comprise volatile and/or non-volatile memory such as random-access memory (RAM), dynamic random access memory (DRAM), static random access memory (SRAM), magnetic media, optical media, nano-media, a hard drive, a compact disk, a digital versatile disc (DVD), optical circuits, and/or other devices configured for storing analog or digital information, such as in a database. A computer-readable medium, as used herein, expressly excludes paper. Computer-implemented steps of the methods noted herein can comprise a set of instructions stored on a computer readable medium that when executed cause the computing system to perform the steps. A computing system programmed to perform particular functions pursuant to instructions from program software is a special purpose computing system for performing those particular functions. Data that is manipulated by a special purpose computing system while performing those particular functions is at least electronically saved in buffers of the computing system, physically changing the special purpose computing system from one state to the next with each change to the stored data.

What is claimed is:

1. A system for making a comprehensive medical determination, the system comprising:

a medical image generator configured to acquire non-invasive medical images of a plurality of anatomical structures of a patient during an imaging session, the medical image generator further configured to adapt generation of the non-invasive medical images based on feedback received from image analysis logic by fine-tuning at least one of (i) image generation, (ii) focus, or (iii) image processing parameters;

a digital storage storing a plurality of non-invasive medical images of the plurality of anatomical structures of the patient;

a microprocessor in communication with the digital storage and configured to implement the image analysis logic comprising a trained neural network, wherein the image analysis logic is further configured to:

process one or more non-invasive medical images of the plurality of non-invasive medical images of the plurality of anatomical structures of the patient to provide a quantitative prediction or an insight related to a medical condition of the patient; and determine a confidence score associated with the quantitative prediction; and a user interface configured to provide the quantitative prediction and the confidence score to a healthcare professional.

2. The system of claim 1, wherein the image analysis logic includes first logic configured to process the one or more non-invasive medical images of the plurality of non-invasive medical images to provide the quantitative prediction related to a current state of the medical condition.

3. The system of claim 1, wherein the image analysis logic includes second logic configured to process the one or more non-invasive medical images of the plurality of non-invasive medical images to provide the quantitative prediction related to a future state, progression, or risk of the medical condition.

4. The system of claim 1, wherein the image analysis logic is configured to employ a regression algorithm to provide the quantitative prediction as a range or confidence interval.

5. The system of claim 1, wherein the image analysis logic is configured to employ a classification algorithm to provide the quantitative prediction as one of a plurality of categories or severities.

6. The system of claim 1, wherein the image analysis logic is further configured to provide the quantitative prediction based on a combination of the non-invasive medical images and additional clinical data.

7. The system of claim 1, wherein the non-invasive medical images are represented by raw image data.

8. A method for training a neural network to make comprehensive medical predictions, the method comprising:

receiving a dataset of non-invasive medical images of a plurality of anatomical structures of a plurality of patients, the non-invasive medical images labeled with ground truth diagnoses of a plurality of medical conditions;

classifying the non-invasive medical images according to views or features included within the non-invasive medical images;

filtering the non-invasive medical images to remove images:

(i) that lack the views or the features that have been determined to have determinative value; and (ii) that are of insufficient quality or resolution;

partitioning the dataset into a training set, a validation set, and an independent test set;

training the neural network using the training set to predict the plurality of medical conditions;

fine-tuning the neural network using the validation set to optimize its performance and generalization; and evaluating final performance characteristics of the neural network using the independent test set, by comparing quantitative predictions based on the independent test set provided by the neural network to ground truth diagnosis labels associated with the independent test set.

9. The method of claim 8, wherein the non-invasive medical images comprise one or more imaging modalities including ultrasound, radiography, MRI, CT, PET, SPECT, mammography, and optical imaging.

10. The method of claim 8, further comprising pre-processing the non-invasive medical images before training the neural network, wherein pre-processing the non-invasive medical images includes one or more of normalization, resizing, cropping, or augmentation.

11. The method of claim 8, further comprising employing transfer learning to leverage pre-trained neural networks and adapting the pre-trained neural networks to perform comprehensive medical condition prediction.

12. The method of claim 8, wherein the non-invasive medical images are represented by raw image data.

13. A method for making a comprehensive medical determination using a trained neural network, the method comprising:

acquiring one or more non-invasive medical images of a plurality of anatomical structures of a patient using an image acquisition device, the image acquisition device configured to adapt generation of the one or more non-invasive medical images based on feedback received from image analysis logic by fine-tuning at least one of (i) image generation, (ii) focus, or (iii) image processing parameters;

pre-processing the acquired non-invasive medical images to optimize the acquired non-invasive medical images for input into the trained neural network;

providing the pre-processed non-invasive medical images to the trained neural network, which has been optimized to predict a plurality of medical conditions;

receiving from the trained neural network a quantitative prediction, and a confidence score associated with the quantitative prediction, related to the presence, absence, severity, or risk of a medical condition for the patient; and presenting the quantitative prediction to a healthcare professional via a user interface to support clinical decision-making.

14. The method of claim 13, wherein the trained neural network employs a combination of regression and classification algorithms to provide both continuous and categorical predictions.

15. The method of claim 13, wherein the quantitative prediction is accompanied by explanations or visualizations highlighting key anatomical features or abnormalities that contributed to the quantitative prediction.

16. The method of claim 13, wherein the trained neural network is continuously updated and refined using new non-invasive medical images and ground truth data.

17. The method of claim 13, wherein the one or more non-invasive medical images are represented by raw image data.

* * * * *